United States Patent [19]

Tsao

[11] 4,028,427

[45] June 7, 1977

[54] AQUEOUS STREAM TREATMENT IN CHLORINATED HYDROCARBON PRODUCTION

[75] Inventor: Utah Tsao, Jersey City, N.J.

[73] Assignee: The Lummus Company, Bloomfield, N.J.

[22] Filed: Aug. 27, 1975

[21] Appl. No.: 608,193

[52] U.S. Cl. .................. 260/659 R; 260/650 R; 260/652 P; 260/654 R; 260/656 R; 260/659 A; 260/662 R

[51] Int. Cl.$^2$ .................. C07C 19/00; C07C 21/04; C07C 25/04

[58] Field of Search ............ 260/659 R, 659 A, 660, 260/662 R, 654 R, 656 R, 650 R, 652 P

[56] References Cited

UNITED STATES PATENTS

| | | |
|---|---|---|
| 2,402,978 | 7/1946 | Allen, Jr. et al. ............ 260/662 R X |
| 2,403,179 | 7/1946 | Hull et al. ...................... 260/660 X |
| 2,433,419 | 12/1947 | Bosko ................................ 260/660 |
| 2,841,243 | 7/1958 | Hooker et al. ............. 260/652 P X |
| 3,148,041 | 9/1964 | Dehn et al. ................. 260/659 A X |
| 3,259,561 | 7/1966 | Sievers .......................... 260/660 X |
| 3,584,066 | 6/1971 | Reni et al. .......................... 260/660 |
| 3,848,007 | 11/1974 | Forlano ..................... 260/658 R X |
| 3,963,584 | 6/1976 | Tsao ............................ 260/652 P X |
| 3,980,723 | 9/1976 | Riegel ........................ 260/652 P X |
| 3,988,383 | 10/1976 | Huang et al. ............. 260/659 A X |

*Primary Examiner*—Daniel E. Wyman
*Assistant Examiner*—Thomas A. Waltz
*Attorney, Agent, or Firm*—Marn & Jangarathis

[57] ABSTRACT

In the production of chlorinated hydrocarbons, a waste water stream is recovered from the effluent and stripped of chlorinated hydrocarbon impurities by the use of a portion of the hydrocarbon to be chlorinated as a stripping gas. In addition, an aqueous hydrogen chloride stream recovered from the chlorinated hydrocarbon effluent can also be stripped of chlorinated hydrocarbon impurities by the use of a portion of the hydrocarbon to be chlorinated as a stripping gas.

10 Claims, 1 Drawing Figure

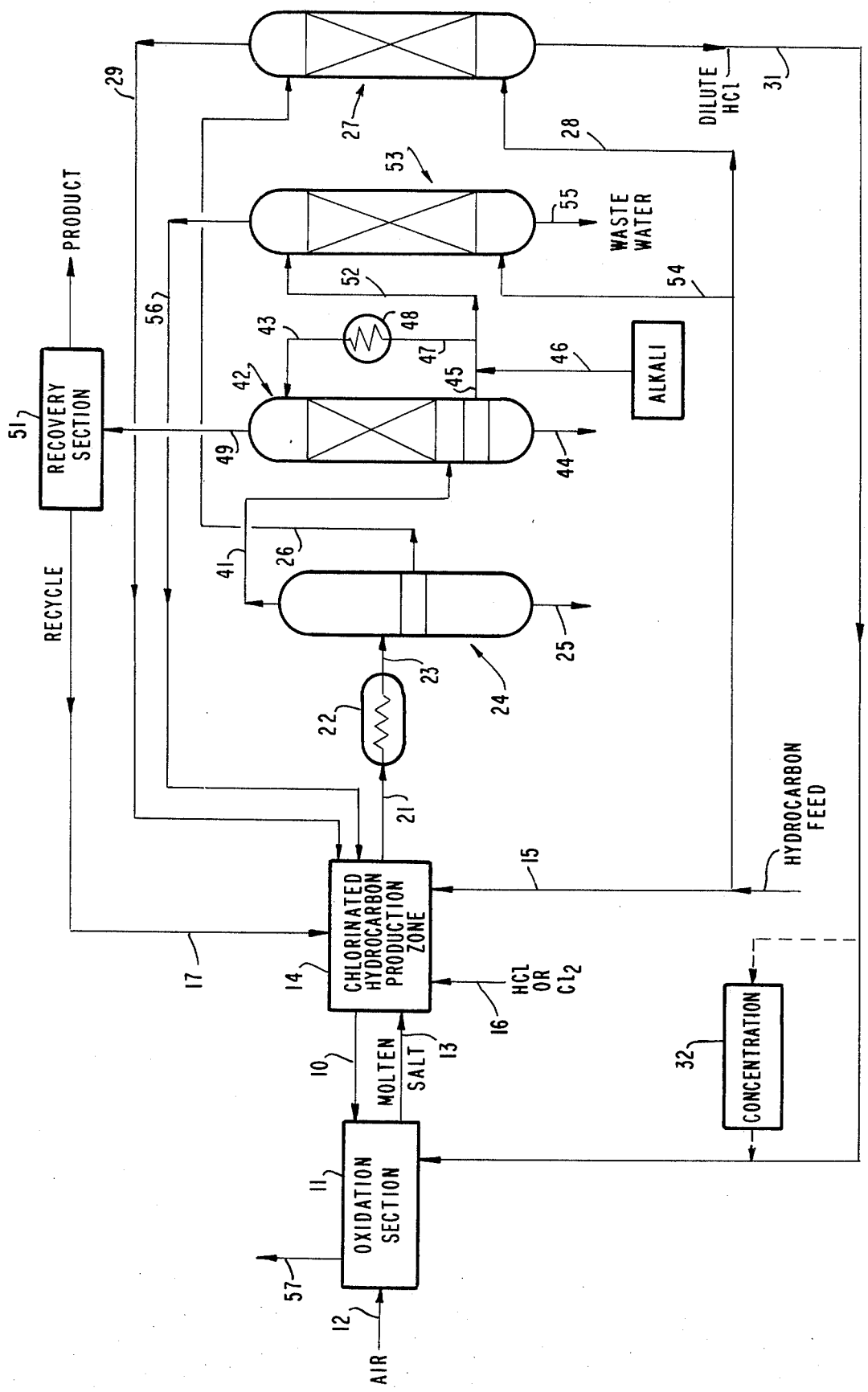

AQUEOUS STREAM TREATMENT IN CHLORINATED HYDROCARBON PRODUCTION

This invention relates to the production of chlorinated hydrocarbons, and more particularly, to the treatment of aqueous streams recovered from a chlorinated-hydrocarbon effluent.

In producing chlorinated hydrocarbons, aqueous steams are recovered from the chlorinated hydrocarbon effluent. It has been found that such streams include chlorinated hydrocarbons as impurities and, accordingly, there is a need for effective separation of such chlorinated hydrocarbon impurities from such aqueous steams.

An object of the present invention is to provide for treatment of aqueous streams recovered from a chlorinated hydrocarbon effluent.

Another object of the present invention is to provide for removal of chlorinated hydrocarbon impurities from a aqueous streams recovered from a chlorinated hydrocarbon effluent.

These and other objects of the present invention should be more apparent from reading the following detailed description thereof.

In accordance with the present invention, a waste water stream is recovered from a chlorinated hydrocarbon production zone, with the waste water stream containing chlorinated hydrocarbon as an impurity. The waste water stream, including chlorinated hydrocarbon impurity, is introduced into a stripping zone along with a portion of the hydrocarbon, employed for the production of chlorinated hydrocarbons, with the hydrocarbon being employed as a stripping gas to strip chlorinated hydrocarbon impurity from the waste water. The stripped waste water is recovered from the stripping zone, and a gas stream, comprised of the stripping gas and stripped chlorinated hydrocarbon, recovered from the stripping zone, is introduced into the chlorinated hydrocarbon production zone.

In accordance with another aspect of the present invention, an aqueous hydrogen chloride solution is recovered from the chlorinated hydrocarbon effluent and the aqueous hydrogen chloride solution, containing chlorinated hydrocarbon impurity, is also introduced into a stripping zone, wherein chlorinated hydrocarbon is stripped from the aqueous hydrogen chloride by the use of the hydrocarbon to be chlorinated, as a stripping gas. The stripping gas, including stripped chlorinated hydrocarbon, is introduced into the chlorinated hydrocarbon production zone.

The stripper for stripping chlorinated hydrocarbon impurities from the waste water stream is operated at temperatures and pressures which are effective for separating the chlorinated hydrocarbon impurities from the water. In general, the stripper is operated at an overhead temperature from about 150° F to about 50° F, preferably an overhead temperature from about 120° F to about 100° F, a bottoms temperature from about 140° F to about 60° F, preferably from about 110° F to about 100° F and a pressure from about 200 psig to about 20 psig, preferably from about 80 psig to about 40 psig. It is to be understood, however, that such temperatures and pressures are only illustrative, and therefore the use of other temperature and pressure conditions is deemed to be within the scope of those skilled in the art from the teachings herein.

The stripping gas is preferably introduced into the stripper in an amount to provide a stripping factor from 1.5 to 4.0. For a stripper operated at about 120° F and 80 psig, the amount of stripping gas required is about 2 mole % of the waste water to be stripped.

In general, the waste water stream contains about 1.0 weight % of chlorinated hydrocarbon impurities and, in accordance with the present invention, the waste water withdrawn from the stripper generally contains no more than 10 ppm, by weight, chlorinated hydrocarbons, and preferably no more than 1 ppm, by weight chlorinated hydrocarbons.

The stripper for stripping chlorinated hydrocarbon impurity from the aqueous hydrogen chloride stream, recovered from the chlorinated hydrocarbon effluent, is operated at temperatures and pressures which are effective for separating chlorinated hydrocarbon from the aqueous hydrogen chloride solution. In general, the stripper for this purpose is operated at an overhead temperature from about 175° F to about 90° F, preferably an overhead temperature from about 150° F to about 100° F, a bottoms temperature from about 165° F to about 90° F, preferably from about 140° F to about 120° F, and a pressure from about 200 psig to about 20 psig, preferably from about 80 psig to about 40 psig. It is to be understood, however, that the hereinabove described conditions are only illustrative, and accordingly, the use of other conditions is deemed to be within the scope of those skilled in the art from the teachings herein.

In general, the stripping gas is introduced in an amount to provide a stripping factor from 1.5 to 4.0. For a stripper operated at about 130° F and 80 psig, the amount of stripping gas required is about 3 mol % of the aqueous hydrogen chloride stream to be stripped.

The aqueous hydrogen chloride stream introduced into the stripper generally contains about 1 weight % of chlorinated hydrocarbon impurities, and in accordance with the present invention, the aqueous hydrogen chloride which is withdrawn from the stripper contains no more than 10 ppm, by weight of chlorinated hydrocarbon, and preferably no more than 1 ppm, by weight of chlorinated hydrocarbon.

The hydrocarbon gas, employed for stripping chlorinated hydrocarbons from the waste water and/or aqueous hydrogen chloride stream can then be introduced into the chlorinated hydrocarbon production reactor, with the chlorinated hydrocarbons then being withdrawn with the chlorinated hydrocarbon effluent. Although it is preferred to employ fresh feed hydrocarbon as the stripping gas, it is to be understood that recycle unreacted hydrocarbon recovered in the chlorinated hydrocarbon separation and recovery section could also be employed as the stripping gas for removing chlorinated hydrocarbon impurities from the waste water and/or aquous hydrogen chloride steam.

Chlorinated hydrocarbon effluent which is treated in accordance with the present invention may be produced by any one of a wide variety of chlorination and/or oxychlorination processes. The net feed for such a process can be any one of a wide variety of hydrocarbons, and as representative examples of such hydrocarbons, there may be mentioned: aromatic hydrocarbons, such as benzene; aliphatic hydrocarbons (saturated or olefinically unsaturated), preferably a $C_1$ to $C_4$ aliphatic hydrocarbon; and the like. The most preferred feeds are ethane, ethylene and methane. Air is also a feed as a source of oxygen.

The present invention is particularly applicable to processes for producing chlorinated $C_2$ hydrocarbons and chlorinated methanes by the use of molten salts, wherein the feed is contacted with hydrogen chloride and/or chlorine and a molten salt containing a multivalent metal chloride in its higher and lower valence state and the oxychloride of the metal (preferably copper chloride and oxychloride).

The teachings of the present invention are also applicable to oxychlorination processes in which a hydrocarbon is directly contacted with oxygen and/or air and hydrogen chloride, as known in the art. In this case, the most preferred stripping gas is the oxygen/air feed.

The invention will be further described with respect to an embodiment thereof illustrated in the accompanying drawing wherein:

The drawing is a simplified schematic flow diagram of an embodiment of the present invention.

It to be understood, however, that the scope of the present invention is not to be limited thereby.

Referring now to the drawing, a molten salt mixture including cuprous chloride, cupric chloride and a melting point depressant, in particular, potassium chloride, in line 10, is introduced into a reaction zone, included in an overall oxidation reaction section, schematically designated as 11. In the oxidation reaction zone the molten salt is contacted with molecular oxygen, generally introduced as air, through line 12 to produce copper oxychloride. The reaction is generally effected at temperatures of from about 600° F to about 900° F.

A molten salt mixture, containing curprous chloride, cupric chloride and copper oxychloride withdrawn from the reaction zone of the oxidation reaction section 11, through line 13, is introduced into a chlorinated hydrocarbon production zone, schematically indicated as 14. In the chlorinated hydrocarbon production zone 14, the molten salt is contacted with a fresh feed hydrocarbon, such as methane, introduced through line 15, hydrogen chloride, chlorine or mixtures thereof, introduced through line 16, and a recycle stream, including unreacted hydrocarbon, and chlorinated hydrocarbon intermediates introduced through line 17 to effect production of chlorinated hydrocarbon; in particular, chlorinated methanes. Zone 14 is generally operated at temperatures in the order of about 700° F to 1000° F, with lower temperatures within the range being preferred for methane feeds.

Molten salt recovered from chlorinated hydrocarbon production zone 14 is recycled through line 10 to the oxidation reaction zone, in the oxidation reaction section 11.

A chlorinated hydrocarbon effluent, including chlorinated hydrocarbon, unreacted hydrocarbon, water vapor, hydrogen chloride, carbon dioxide and non-condensibles, in line 21, is passed through a condenser 22 wherein the effluent is indirectly cooled to a temperature, which effects condensation of an aqueous hydrogen chloride solution, and in addition, some chlorinated hydrocarbon. The cooled effluent, in line 23, is introduced into a separator 24, wherein the condensed portion is separated into an organic phase, comprising chlorinated hydrocarbon, and an aqueous phase of dilute hydrochloric acid. The condensed organic phase is withdrawn from separator 24 through line 25 and may be employed, jif desired, as a quench liquid in the chlorinated hydrocarbon production zone.

The condensed aqueous phase is withdrawn from separator 24 through line 26 and introduced into a stripper 27, designed and operated to effect stripping of chlorinated hydrocarbon impurities therefrom. A portion of the net hydrocarbon feed for the chlorinated hydrocarbon production zone, in line 28, is introduced into the lower portion of stripping column 27 to effect stripping of chlorinated hydrocarbon impurities from the dilute aqueous hydrogen chloride.

A gaseous overhead, containing hydrocarbon, introduced as stripping gas, and stripped chlorinated hydrocarbon, is withdrawn from stripping column 27 through line 29 and introduced into the chlorinated hydrocarbon production zone 14. In this manner, a portion of the net feed to the chlorinated hydrocarbon production zone is employed to provide stripping requirements for stripping chlorinated hydrocarbon impurities from an aqueous hydrogen chloride stream recovered from the net chlorinated hydrocarbon production effluent.

A dilute aqueous hydrogen chloride solution is withdrawn from the bottom of stripping column 27 through line 31, and such dilute aqueous hydrogen chloride stream, may be introduced into the oxidation reaction zone, included in the oxidation section 11, in order to effect recovery of chlorine values. If desired and/or required, the dilute hydrogen chloride stream in line 31 may be concentrated in a zone 32, prior to being introduced into the oxidation reaction section. Alternatively, concentration of the dilute hydrogen chloride stream may be effected in the quenching section of the oxidation reaction section 11. Insome cases, however, the aqueous hydrogen chloride stream recovered in line 31 may be directly introduced into the oxidation reactor, in oxidation section 11, without prior concentration.

The uncondensed portion of the chlorinated hydrocarbon effluent, containing unreacted hydrocarbon, chlorinated hydrocarbon, water vapor, hydrogen chloride, carbon dioxide etc., is withdrawn from separator 24 through line 41 and introduced into a direct contact quench vessel 42.

In quench vessel 42, the gaseous effluent is directly contacted with an aqueous quench liquid, introduced through line 43, to indirectly cool the effluent and condense additional water vapor therefrom. In addition, some chlorinated hydrocarbon is also condensed from the effluent. The condensed portion forms an aqueous phase and an organic phase in the bottom of the quench tower 42.

The condensed organics, recovered from quench tower 42, through line 44, may be employed as a quench liquid in the chlorinated hydrocarbon production zone.

The condensed aqueous phase is withdrawn from quench tower 42 through line 45, and is preferably combined with alkali, such as sodium hydroxide, in line 46 in order to maintain alkaline conditions in the aqueous phase.

A first portion of the aqueous phase is passed through line 47, including quench cooler 48, wherein the aqueous phase is cooled to a temperature suitable for providing the cooling requirement for quench tower 42. The cooled quench liquid is introduced into tower 42 through line 43.

The uncondensed portion of the chlorinated hydrocarbon effluent is withdrawn from quench tower 42 through line 49 and introduced into a recovery section 51 to recover net chlorinated hydrocarbon product, unreacted hydrocarbon, and intermediate chlorinated hydrocarbon for recycle to the chlorinated hydrocarbon production zone. In addition, the recovery section may include apparatus for separating carbon dioxide and inerts from the net chlorinated hydrocarbon effluent.

The remaining portion of the aqueous phase withdrawn from tower 42, in line 52, is introduced into a stripping tower, schematically designated as 53, designed and operated to strip chlorinated hydrocarbon impurities from the water. A portion of the net hydrocarbon feed, in line 54, is introduced into the bottom of stripping tower 53 to provide the stripping requirements therefor.

A waste water stream, essentially free of chlorinated hydrocarbon impurities, is withdrawn from the bottom of stripping tower 53 through line 55. This waste water stream containing some sodium bicarbonate and very small amount of dissolved hydrocarbon can be used to neuttralize the vent gas stream 57 from the oxidation section 11 before it is discharged to the atmosphere.

An overhead, comprised of hydrocarbon feed, introduced as stripping gas, and stripped chlorinated hydrocarbon, is withdrawn from tower 53 through line 56 and introduced into the chlorinated hydrocarbon production zone 14. In this manner, the stripping requirements for stripping chlorinated hydrocarbon impurities from a waste water stream is provided by a portion of the net hydrocarbon feed to the chlorinated hydrocarbon production zone.

Numerous modifications and variations of the hereinabove described embodiments are deemed to be within the scope of the present invention.

Thus, for example, the dilute aqueous hydrogen chloride withdrawn from separation vessel 24 through line 26 can be introduced into a hydrogen chloride concentration column, wherein water, including chlorinated hydrocarbon impurities, is stripped from the aqueous hydrogen chloride, to provide a more concentrated aqueous hydrogen chloride solution. In such an embodiment, the overhead withdrawn from the hydrogen chloride concentration column, includes chlorinated hydrocarbon impurities, and all or a portion of the overhead can be condensed and introduced into the water stripping column 53 to strip the chlorinated hydrocarbon impurities therefrom.

As a further alternative, the chlorinated hydrocarbons can be produced other than by the preferred molten salt technique.

As still another modification, the waste water stream and dilute aqueous hydrogen chloride can be recovered other than by condensation as particularly described.

As still another modification, instead of using fresh hydrocarbon feed for effecting stripping of chlorinated hydrocarbon impurities from the aqueous steams, unreacted hydrocarbon, recovered for recycle in the recovery section or air/oxygen used in the oxychlorination reaction can be employed for providing all or a portion of the stripping requirements.

Similarly, although the hereinabove embodiment has been particularly described with respect to the production of chlorinated methanes, the embodiment is equally applicable to the production of other chlorinated hydrocarbons. In such cases, the hydrocarbon to be employed as a feed to the chlorinated hydrocarbon production zone, whether fresh feed or recycle unreacted hydrocarbon, is employed to provide stripping requirements for stripping chlorinated hydrocarbon impurities from the water and/or hydrogen chloride stream recovered from the chlorinated hydrocarbon effluent. As should be apparent to those skilled in the art, the chlorinated hydrocarbon(s) generally present as impurities and the hydrocarbon used as stripping gas have a number of carbon atoms corresponding to the number of carbon atoms in the net hydrocarbon feed.

The invention will be further described with respect to the following examples thereof; however, it is to be understood that the scope of the invention is not to be limited thereby:

EXAMPLE I

In the manufacture of chlormethanes in accordance with the embodiment of the drawing, an aqueous hydrogen chloride solution is recovered from the quench recovery section. the temperature of this stream is about 150° F. This stream is stripped with the fresh methane feed gas in a stripper operated at 50 psig. The flow rate and composition of this stream and the phase equilibrium constants of the chlorinated hydrocarbons are as follows:

| Components | Mol/hr | lb/hr | Equilibrium Constant at 150° F & 50 psig |
|---|---|---|---|
| HCl | 5.08 | 185 | — |
| $H_2O$ | 109.15 | 1967 | — |
| $CH_3Cl$ | Trace | Trace | 5,050 |
| $CH_2Cl_2$ | 0.05 | 4 | 181 |
| $CHCl_3$ | 0.08 | 10 | 231 |
| $CCl_4$ | 0.01 | 2 | 1,665 |
| | 114.37 | 2.168 | |

Based upon equilibrium constants, methylene chloride is the most difficult component to be stripped from the solution. If a stripping factor of 3 is selected, the required methane stripping gas is 1.9 mol/hr, whereas the total, fresh methane feed gas is 109 mol/hr. Therefore, a plentiful supply of stripping gas is available. If six equilibrium stages are provided in the stripper, a stripping efficiency of 99.9% can be achieved. The methylene chloride remaining in the stripped solution will be reduced to 2 ppm by weight.

EXAMPLE II

In the same process, a neutralized waste water stream at 110° F is recovered. The flow rate and composition of this stream and the phase equilibrium constants of the chlorinated hydrocarbons are as follows:

| Components | Mol/hr | lb/hr | Equilibrium Constants at 110° F & 65 psia |
|---|---|---|---|
| $H_2O$ | 42.56 | 767 | — |
| $CH_3Cl$ | 0.01 | 1 | 1,760 |
| $CH_2Cl_2$ | 0.06 | 5 | 85 |
| $CHCl_3$ | 0.02 | 2 | 103 |
| $CCl_4$ | Trace | Trace | — |
| $NaHCO_3$ | 0.08 | 7 | — |
| | 42.73 | 782 | |

Using the same stripping factor and the same number of equilibrium stages in the stripper as the aqueous hydrogen chloride stripper of Example I, the required methane stripping gas is 1.3 mol/hr and the methylene chloride remaining in the stripped waste water will be 6 ppm by weight.

The present invention is particularly advantageous in that chlorinated hydrocarbon impurities can be effectively removed from aqueous streams recovered from a chlorinated hydrocarbon effluent. In addition, by employing the hydrocarbon to be chlorinated to provide stripping requirements, such removal of chlorinated hydrocarbon impurities can be effected with reduced utilities requirements.

Numerous modifications and variations of the present invention are possible in light of the above teachings, and, therefore, the invention may be practiced, within the scope of the appended claims, otherwise than as particularly described.

What is claimed is:

1. In a process for the production of chlorinated hydrocarbons from a hydrocarbon wherein a chlorinated hydrocarbon effluent including water vapor is withdrawn from a chlorinated hydrocarbon production zone, the improvement comprising:

recovering waste water from the chlorinated hydrocarbon effluent, said waste water including chlorinated hydrocarbons as impurities;

stripping chlorinated hydrocarbons from the waste water, said stripping being effected with a stripping gas comprising a portion of the feed to the chlorinated hydrocarbon production zone selected from the group consisting of hydrocarbon and oxygen containing gas;

recovering stripped waste water;

recovering stripping gas and stripped chlorinated hydrocarbon impurities; and introducing said recovered stripping gas and chlorinated hydrocarbon impurities into the chlorinated hydrocarbon production zone.

2. The process of claim 1 wherein the stripping is effected at an overhead temperature of from about 50° F to about 150° F, a bottoms temperature of from about 60° F to about 140° F and a pressure of from about 20 to about 200 psig.

3. The process of claim 1 wherein the stripping gas comprises a portion of the hydrocarbon feed to the chlorinated hydrocarbon production zone.

4. The process of claim 3 wherein the hydrocarbon stripping gas is methane.

5. The process of claim 3 wherein the hydrocarbon stripping gas is a $C_2$ hydrocarbon.

6. The process of claim 3 and further comprising recovering from the chlorinated hydrocarbon effluent an aqueous hydrogen chloride solution, said aqueous hydrogen chloride solution containing chlorinated hydrocarbon impurities; stripping chlorinated hydrocarbon impurities from the aqueous hydrogen chloride solution, said stripping being effected wth additional stripping gas, comprising an additional portion of the hydrocarbon feed to the chlorinated hydrocarbon production zone; recovering stripped aqueous hydrogen chloride; recovering the additional stripping gas, including chlorinated hydrocarbon impurities; and introducing the additional stripping gas, including chlorinated hydrocarbon impurities into said chlorinated hydrocarbon production zone.

7. The process of claim 6 wherein the stripping of chlorinated hydrocarbon from the aqueous hydrogen chloride is effected at an overhead temperature of from about 90° F to about 175° F, a bottoms temperature of from about 90° F to about 165° F and a pressure of from about 20 to about 200 psig.

8. The process of claim 7 wherein the stripping gas and additional stripping gas are both methane.

9. The process of claim 7 wherein the stripping gas and additional stripping gas are both a $C_2$ hydrocarbon.

10. The process of claim 1 wherein chlorinated hydrocarbons are produced by direct oxychlorination of hydrocarbon feed with hydrogen chloride and an oxygen-containing gas and the stripping gas is a portion of the oxygen-containing gas.

* * * * *